United States Patent [19]

Crisp et al.

[11] Patent Number: 4,925,495
[45] Date of Patent: May 15, 1990

[54] WASHING APPARATUS AND METHOD

[75] Inventors: William E. Crisp, Phoenix; Melvyn Engel, Scottsdale; Richard C. Kudlicki; Judson L. Smith, both of Tempe, all of Ariz.

[73] Assignee: Scientific Growth, Inc., Tempe, Ariz.

[21] Appl. No.: 147,369

[22] Filed: Jan. 25, 1988

[51] Int. Cl.⁵ ............................................. B08B 7/04
[52] U.S. Cl. ...................................... 134/18; 134/26; 134/56 R; 134/95; 134/112
[58] Field of Search .............. 134/26, 36, 56 R, 57 D, 134/57 R, 95, 113, 18

[56] References Cited

U.S. PATENT DOCUMENTS

| | | | |
|---|---|---|---|
| 3,220,424 | 11/1965 | Nelson | 134/113 |
| 3,639,844 | 2/1972 | Karklys | 134/57 D |
| 3,699,984 | 10/1972 | Davis | 134/95 |
| 3,757,806 | 9/1973 | Bhaskar et al. | 134/36 |
| 3,881,328 | 5/1975 | Kleimola et al. | 134/95 |
| 3,918,987 | 11/1975 | Kopfer | 134/95 |
| 4,001,599 | 1/1977 | Karklys | 134/57 D |
| 4,219,367 | 8/1980 | Cary et al. | 134/36 |
| 4,688,585 | 8/1987 | Vetter | 134/56 R |

Primary Examiner—Asok Pal
Assistant Examiner—Ourmazd S. Ojan
Attorney, Agent, or Firm—Cahill, Sutton & Thomas

[57] ABSTRACT

Method and apparatus for periodically cleaning washing apparatus in which washing liquid is intermittently circulated through a washing chamber adapted to contain the hand of a user. Cleaning is accomplished by intermittently circulating a cleaning liquid through the chamber while displaying a warning to potential users to not use the apparatus during the cleaning cycle. Cleaning is initiated (a) when the apparatus has been used for hand washing a predetermined number of times, (b) a predetermined period of time has elapsed since the last cleaning cycle, (c) the apparatus has been serviced, or (d) following interruption of the electrical power supply to the apparatus.

14 Claims, 1 Drawing Sheet

U.S. Patent | May 15, 1990 | 4,925,495
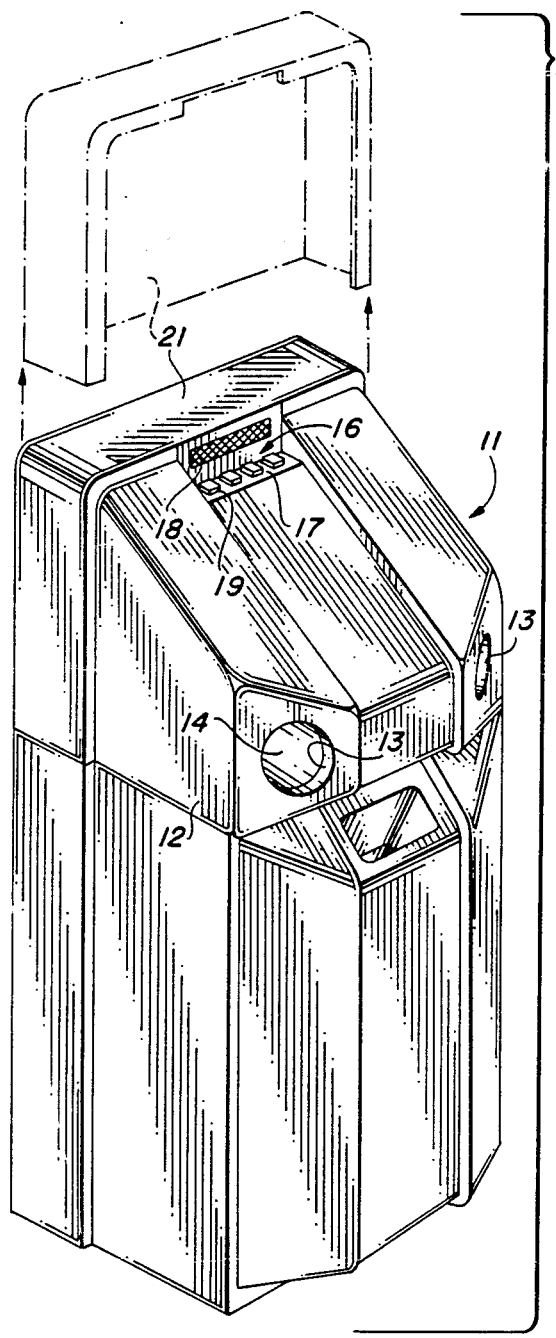
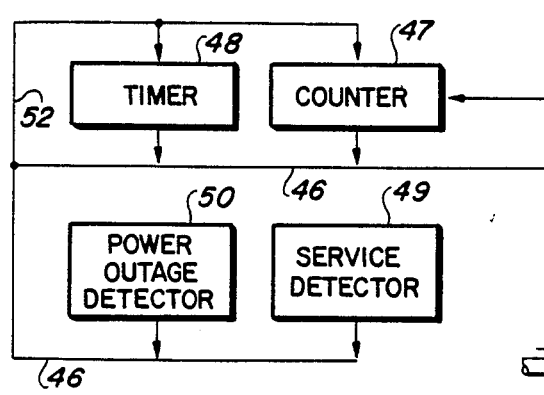
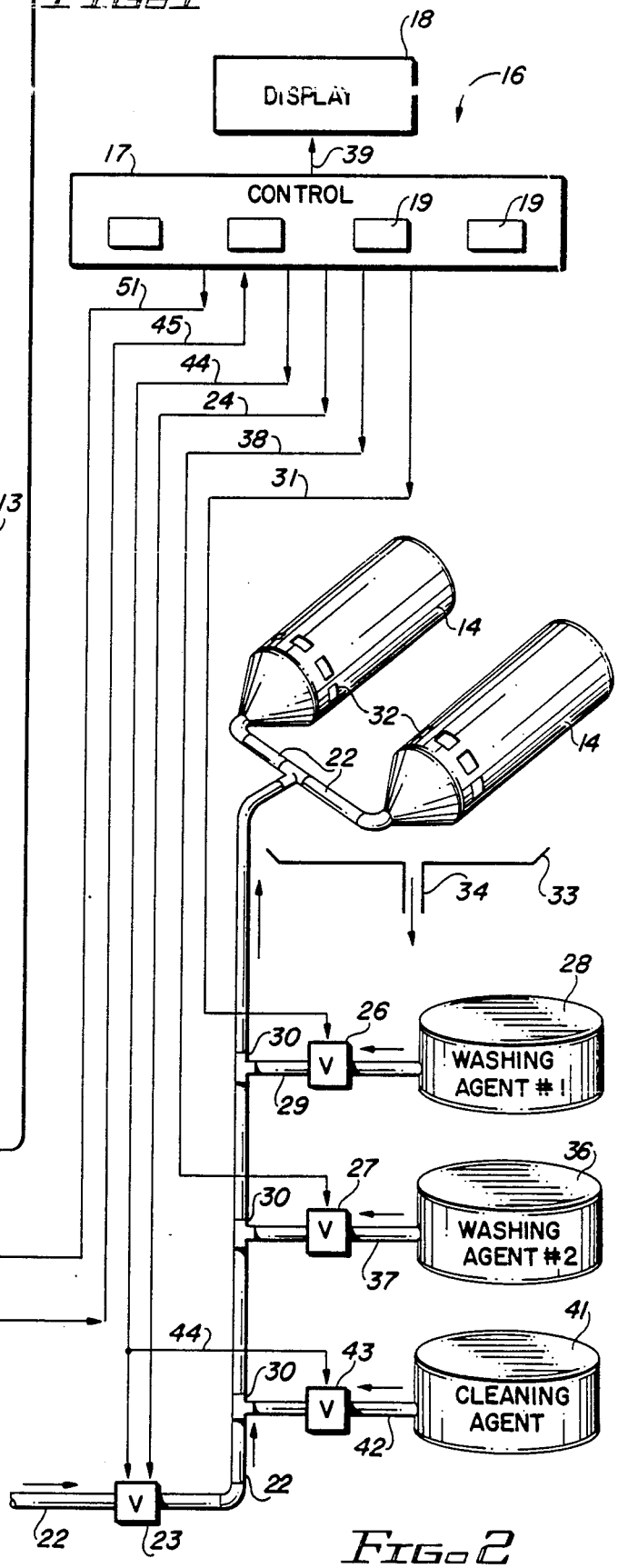
FIG-1
FIG-2

WASHING APPARATUS AND METHOD

TECHNICAL FIELD

This invention is concerned with improving the performance of apparatus for washing human body parts, such as hands, hands and arms and feet. The invention is particularly useful in apparatus for washing the hands of a person working in environments requiring cleanliness.

BACKGROUND ART

Various pieces of apparatus have been devised for washing the hands, or hands and forearms, of persons, such as surgeons and others, who work in clean and sterile environments. Co-pending application for U.S. patent Ser. No. 112,299, filed Oct. 26, 1987, U.S. Pat. No. 4,817,651, by W. E. Crisp et al for "HAND AND FOREARM CLEANSING APPARATUS", which is assigned to the same assignee as the present application, discloses apparatus which is particularly effective for this purpose. That patent application discloses and evaluates other patented apparatus in this same field. The disclosure of the Crisp et al. application is incorporated herein by reference as illustrative background art.

In the apparatus disclosed in the aforementioned Crisp et al. patent application, hand washing is accomplished by circulating a washing liquid through washing chambers into which the user inserts his or her hands. The apparatus has user manipulated controls by which the user determines the type of washing agent to be employed, possibly the sequence of application of various washing agents, and initiates the washing cycle.

One might think that the periodic, repetitive operation of hand washing apparatus of this type would keep the apparatus clean. In other words, you would not have to periodically clean the apparatus itself in a procedure or cycle separate and apart from the usual washing cycles. However, it has been observed that there are certain normal and abnormal operating conditions which make it desirable to clean the apparatus itself to insure its capability of effectively washing hands.

In the normal operation of hand washing apparatus transient bacteria is removed from the user's skin. Not all of this bacteria is flushed from the washing chamber and, with repeated washing operations, a significant quantity of such bacteria may build up in the washing apparatus. If this build up is allowed to continue it is possible for the bacteria level to reach the point where the user's hands can become contaminated rather than cleaned or only partially cleaned during washing. Thus, the performance of the washing apparatus can become impaired.

Such undesirable build up of bacteria could possibly be prevented by incorporating more powerful washing agents in the hand washing cycles. This generally is not feasible because the skin of many users could not tolerate the more powerful agents required to destroy the bacteria.

It is also possible for bacteria to actually grow within the washing apparatus. Thus, over time, particularly if the apparatus is used infrequently, an objectionable build up of bacteria may occur.

Another normal operating condition which can contribute to a build up of bacteria or other contamination of the washing apparatus is the servicing of the apparatus. This usually requires that the interior of the apparatus be invaded by the hands of a service person and those hands may be particularly unclean and capable of imparting infectious agents into the apparatus.

And, lastly, at least one abnormal operation of the apparatus can lead to an undesirable build up of bacteria in the apparatus. Interruption of electrical power to the apparatus is such a condition. Any prolonged power interruption which prevents the apparatus from going through normal wash cycles leaves the apparatus vulnerable to growth and build up of bacteria therein.

There is a need, therefore, for appropriate apparatus and methods for cleaning the washing apparatus periodically to stem the build up of bacteria likely to be caused by any of the aforementioned normal and abnormal operating conditions.

DISCLOSURE OF THE INVENTION

This invention envisions, first, a method and apparatus for counting the number of times washing liquid is circulated through a washing chamber in normal washing cycles and for initiating a cleaning cycle to circulate cleaning liquid through the washing chamber when a predetermined number of washing cycles have been performed. The cleaning liquid used is of a strength and character to destroy bacteria in the washing apparatus and, as such, preferably is not allowed to contact the skin of a user or potential user of the apparatus. With this in mind, the invention further envisions a method and apparatus for displaying a warning to a potential user to not use the apparatus while the cleaning liquid is being circulated.

The invention also contemplates a method and apparatus for measuring the period of time which has elapsed since the apparatus was last cleaned and for initiating a cleaning cycle when a predetermined period of time has elapsed. Further, the invention involves a method and apparatus for detecting when the apparatus has been serviced and for thereafter initiating a cleaning cycle. Lastly, the invention involves a method and apparatus for monitoring the supply of electrical power to the washing apparatus and for initiating a cleaning cycle in response to re-establishment of electrical power following any interruption thereof.

BRIEF DESCRIPTION OF THE DRAWINGS

The invention is described in greater detail hereinafter by reference to the accompanying drawing wherein:

FIG. 1 is a three-quarter, front, perspective view from above of a hand washing unit utilizing this invention; and FIG. 2 is a schematic diagram illustrating the methods and apparatus of the invention.

BEST MODE FOR CARRYING OUT THE INVENTION

In FIG. 1 reference number 11 designates generally a free-standing hand washing apparatus the components of which are housed in a cabinet 12. This apparatus is intended to be installed in hospitals or other locations where employees or occupants are required periodically to wash their hands.

The cabinet 12 has a pair of openings 13 in the front thereof through which the hands, and possibly the forearms, of a user can be inserted into washing chambers 14 inside the cabinet.

Cabinet 12 also has on the exterior thereof a control center, indicated generally by numeral 16, which comprises a user manipulated control unit 17 and a display 18. Control unit 17 has a plurality of push buttons 19 thereon. By manipulating buttons 19 the user controls the number and type of washing agents used in washing his or her hands, their sequence of application and possibly the duration of the washing sequence. Manipulation of the control unit 17 by a user of course initiates the hand washing cycle of operation which includes a time delay to allow the user to remove his hand from the control unit and place it in a washing chamber 14.

Cabinet 12 also preferably has a removable cover 21 as a portion thereof permitting access to the interior of the apparatus for servicing purposes.

The mechanical features of hand washing apparatus 11 by which effective washing of the hands of a user is accomplished can be like those disclosed in the aforementioned Crisp et al. patent application and the prior patents cited therein.

The present invention is primarily concerned with methods and apparatus for periodically performing a cleaning operation, or cycle, for the apparatus in response to certain normal and abnormal operating conditions which possibly could result in an undesirable build up of bacteria within the apparatus. The methods and apparatus for accomplishing this are illustrated schematically in FIG. 2.

In normal washing operations, or cycles, washing liquid is circulated through washing chambers 14. One component of the washing liquid is warm water which is supplied from a source (not shown) through a conduit 22 connected to the washing chambers 14. The direction of water flow is indicated by block arrows along conduit 22.

The flow of water through conduit 22 is under the control of a valve 23 in conduit 22. Valve 23 is opened to initiate the flow of water through conduit 22 in response to a signal from control unit 17 transmitted over control lead 24.

Also under control of control unit 17 are a pair of valves 26 and 27 which control the addition of washing agents to wash water flowing through conduit 22. Valve 26 controls the flow of washing agent #1 from a supply container 28 through a supply conduit 29 which connects with water conduit 22 at a mixing fitting 30. Valve 26 is opened to permit the flow of washing agent #1 into conduit 22 in response to a signal from control unit 17 transmitted over control lead 31. When valves 23 and 26 are opened at the same time under control of control unit 17 washing liquid comprising a mixture of warm water and washing agent #1 is circulated through washing chambers 14. In other words, valves 23 and 26, conduits 22 and 29, and container 28 comprise means for circulating washing liquid through washing chambers 14.

The flow of washing liquid within the chambers 14 takes the form of a spray intended to impinge on all portions of the hands of the user. Washing liquid exits washing chambers 14 through openings 32 therein, is collected in a pan, or sump, 33 and conveyed away by a drain conduit 34.

Valve 27 controls the flow of washing agent #2 from supply container 36 through supply conduit 37 which also connects with water conduit 22 via a mixing fitting 30. Valve 27 is opened in response to a signal from control unit 17 transmitted over control lead 38. When valves 23 and 27 are opened at the same time, washing liquid consisting of a mixture of warm water and washing agent #2 is circulated through washing chambers 14.

By manipulation of push buttons 19 on control unit 17 the user can select the type of liquid to be circulated through washing chambers 14 and the sequence thereof. For example, the user can select a washing liquid including either washing agent #1 or washing agent #2. The washing cycle is usually completed with a rinse operation in which valve 23 is opened and valves 26 and 27 are both closed to circulate water only through chambers 14. Control unit 17 can be preprogrammed to cause the rinse operation to be performed.

Control unit 17 also sends control signals to display 18 over control lead 39. Display 18 preferably is an alpha-numeric LED unit capable of presenting visible messages to a user or potential user under the control of control unit 17. For example, when the washing apparatus is in stand-by condition ready for use, control unit 17 can cause the display 18 to present a sequence of messages such as "SYSTEM READY", "SELECT WASHING AGENT", "AGENT NO. 1-NAME" and "AGENT NO. 2-NAME". Following selection of the desired washing agent by the user, which is done by manipulating appropriate push buttons 19, the control unit 17 can instruct display 18 to present a message indicating start of the wash cycle, such as, "INSERT HANDS NOW" and "WASHING CYCLE COMMENCES IN 8 SECONDS". At the end of the washing cycle the display will be caused to present an appropriate termination message, such as, "WASHING CYCLE COMPLETED".

Because the washing agents dispensed from supply containers 28 and 36 are intended to contact the skin of the user of the apparatus they must be selected from chemical substances which will assist in removing surface bacteria from the skin but which will have no deleterious effect on the skin. This dictates that the washing agents will generally be mild soaps, surfactants, or possibly germicides. Such substances generally do not have the capability of actually destroying bacteria so it is possible, as mentioned previously, for bacteria to build up within the washing apparatus to an undesirable level. This invention prevents that build up from occurring.

The invention provides methods and apparatus for periodically circulating a cleaning liquid through the washing chambers 14 and associated apparatus in response to signals generated by other apparatus which monitor certain normal and abnormal operations of the washing apparatus 11. The apparatus, or means, for supplying the cleaning liquid comprises a cleaning agent supply container 41 which is connected to another mixing fitting 30 in water conduit 22 by cleaning agent supply conduit 42 having a valve 43 therein. When valves 43 and 23 are opened a mixture of water and cleaning agent from container 41 is circulated through washing chambers 14, onto pan 33 and out through drain conduit 34.

The cleaning agent and container 41 should be sufficiently strong to destroy bacteria in and around washing chambers 14. A concentrated chlorine solution is ideal for this purpose. Because of the harshness of such a cleaning agent it is important that a user of the apparatus not insert his hand into one of the washing chambers 14 when the cleaning liquid is being circulated therethrough. And, indeed, according to this invention, the potential user is warned to not use the apparatus during this cleaning cycle. The method and apparatus for creating the warning are described hereinafter.

A cleaning operation is initiated by opening valves 23 and 43 in response to a signal received by these valves over a control lead 44. Control lead 44 is connected to control unit 17 which is, in turn, connected by lead 45 to a control bus 46 capable of transmitting to leads 45 and 44 signals originating from counter means 47, timer means 48, service detector means 49 and power outage detector means 50.

Counter means 47 employs a mechanism for counting the number of times a washing cycle has been performed and for generating a signal over bus 46, lead 45, through control unit 17 to control lead 44 to initiate a cleaning cycle when a predetermined number has been counted. If desired, counter means 47 can be adjustably programmed to initiate a cleaning cycle after, say, 25, 50 or even 100 washing cycles have been performed. The frequency of initiation of cleaning cycles will depend upon the environment in which the hand washing apparatus is used with more frequent cycles being employed when a higher degree of bacteria free washing is required. Counter means 47 receives a signal from control unit 17 over lead 51 each time control unit 17 initiates a washing cycle. Counter means 27 counts the number of signals thereby received from the control unit 17.

Timer means 48 employs a clock, or timer, mechanism for measuring the time that has elapsed since the apparatus has undergone a cleaning cycle and generates a signal over bus 46, through control unit 17 to control lead 44 whenever a predetermined time has elapsed. Timer means 48 can, if desired, be adjustably programmed to generate the cleaning initiate signal after any desired elapsed period of, say, 8, 12, 24 or more hours, again depending upon the environment in which the washing apparatus is used.

Both counter means 47 and timer means 48 are required to be reset to "zero" each time a cleaning cycle is performed. Reset to zero is accomplished by conveying any cleaning initiate signal in bus 46 back to the timer means 48 and the counter means 47 via a reset lead 52.

Service detector means 49 monitors the condition of apparatus 11 and generates a cleaning initiate signal in bus 46, through control unit 17 to control lead 44 whenever the apparatus has been serviced, such as, for replenishment of a washing agent in one of the containers 28 or 36. Servicing of the washing apparatus 11 normally requires that the service person access the interior of the cabinet 12. Access is gained by the removal of cover 21. One convenient way of operating the service detector means 49 is to have it respond to movement of cover 21. Once detector means 49 detects that the cover 21 has been removed and replaced the detector means then generates a cleaning initiate signal.

Power outage detector means 50 monitors the supply of electrical current to the washing apparatus. Detector means 50 generates a signal over bus 46, to control unit 17 to control lead 44 to initiate a cleaning cycle whenever a discontinuity and reestablishment of power is detected.

As mentioned previously, a potential user of the hand washing apparatus 11 should be warned to not use the apparatus during a cleaning cycle, regardless of whether the cleaning cycle has been initiated by the counter means 47, the timer means 48, the service detector means 49 or the power outage detector means 50. A method and apparatus for producing this warning includes display 18. Whenever a cleaning initiate signal is impressed on bus 46 and conveyed to control unit 17 via lead 45 the control unit conveys another signal over lead 39 to display 18 to present a warning to potential users. For example, the display can be caused to present a message, such as, "SELF-CLEANING * DO NOT USE *". Control unit 17 is programmed to terminate the cleaning cycle after a predetermined period of time sufficient to clean the washing chambers 14 and associated apparatus. Cleaning cycle duration can be as little as fifteen seconds. Of course, when the control unit 17 terminates the cleaning cycle by signaling to close valves 23 and 43, the control unit also signals the display 18 to terminate the warning message and present a "SYSTEM READY" message.

From the foregoing it should be apparent that this invention provides effective methods and apparatus for periodically cleaning washing apparatus to insure efficient operation of the latter.

What is claimed is:

1. A method of operating washing apparatus having a washing chamber adapted to receive a portion of a human body, comprising the steps of:
   (a) circulating a washing liquid through the washing chamber to provide a washing cycle for said portion of the body under control of a user of the unit;
   (b) counting the number of times step (a) is performed; and
   (c) circulating an apparatus cleaning liquid through the chamber when step (a) has been performed a predetermined number of times.

2. The method of claim 1 further characterized in that concurrently with the performance of step (c) a warning is displayed to a potential user to not use the apparatus.

3. A method of operating washing apparatus having a washing chamber adapted to receive a portion of a human body, comprising the steps of:
   (a) circulating a washing liquid through the washing chamber to provide a timed washing cycle for said portion of the body under control of a user of the unit; and
   (b) periodically at timed intervals substantially in excess of the time for a washing cycle circulating an apparatus cleaning liquid through the chamber.

4. The method of claim 3 further characterized in that concurrently with the performance of step (b) a warning is displayed to a potential user to not use the apparatus.

5. A method of operating washing apparatus having a washing chamber adapted to receive a portion of a human body, comprising the steps of:
   (a) circulating a washing liquid with a washing agent therein through the washing chamber to provide a washing cycle for said portion of the body under control of a user;
   (b) detecting the servicing of the apparatus; and
   (c) circulating an apparatus cleaning liquid through the chamber following detecting of such servicing.

6. The method of claim 5 further characterized in that concurrently with the performance of step (c) a warning is displayed to a potential user to not use the apparatus.

7. A method of operating washing apparatus having a washing chamber adapted to receive a portion of a human body, comprising the steps of:
   (a) circulating a washing fluid through the washing chamber to provide a washing cycle for said portion of said body under control of a user;
   (b) detecting the occurrence of a discontinuity of electrical power supplied to the apparatus; and (c) circulating an apparatus cleaning liquid through the chamber following detection of such a discontinuity.

8. The method of claim 7 further characterized in that concurrently with the performance of step (c) a warning is displayed to a potential user to not use the apparatus.

9. A method of operating washing apparatus having a washing chamber adapted to receive a portion of a human body comprising the steps of:
 (a) circulating a washing liquid through said chamber to provide a washing cycle for said portion of the body under control of a user;
 (b) counting by means of a counting mechanism the number of times step (a) is performed and initiating a signal when a predetermined number has been reached;
 (c) measuring by means of a timing mechanism the length of time which has elapsed since the apparatus was last cleaned and for initiating a signal when a predetermined period of time has been measured; and
 (d) circulating an apparatus cleaning liquid through said chamber in response to either of the signals generated in step (b) or step (c).

10. The method of claim 9 further characterized in that concurrently with the performance of step (d) a warning is displayed to a potential user to not use the apparatus.

11. The method of claim 9 further characterized in that the counting mechanism for step (b) and the timing mechanism for step (c) are reset to zero upon the performance of step (d).

12. A method of operating washing apparatus having a washing chamber adapted to receive a portion of a human body comprising the steps of:
 (a) circulating a washing liquid with a washing agent therein through the washing chamber to provide a washing cycle for said portion of said body under control of a user;
 (b) counting by means of a counting mechanism the number of times step (a) is performed and initiating a signal when a predetermined number has been reached;
 (c) measuring by means of a timing mechanism the length of time which has elapsed since the apparatus was last cleaned and for initiating a signal when a predetermined period of time has been measured;
 (d) monitoring the servicing of the apparatus and initiating a signal when such servicing is detected;
 (e) monitoring the supply of electrical power to the apparatus and initiating a signal when a discontinuity of power is detected; and
 (f) circulating an apparatus cleaning fluid through said chamber in response to any of the signals generated in steps (b), (c), (d) or (e).

13. The method of claim 12 further characterized in that concurrently with the performance of step (f) a warning is displayed to a potential user to not use the apparatus.

14. The method of claim 12 further characterized in that the counting mechanism for step (b) and the timing mechanism for step (c) are reset to zero upon the performance of step (f).

* * * * *